United States Patent
Guisan et al.

(10) Patent No.: US 10,401,464 B2
(45) Date of Patent: Sep. 3, 2019

(54) SCANNING FERROMAGNETIC RESONANCE (FMR) FOR WAFER-LEVEL CHARACTERIZATION OF MAGNETIC FILMS AND MULTILAYERS

(71) Applicant: Taiwan Semiconductor Manufacturing Company, Ltd., Hsinchu (TW)

(72) Inventors: Santiago Serrano Guisan, San Jose, CA (US); Luc Thomas, San Jose, CA (US); Son Le, Gilroy, CA (US); Guenole Jan, San Jose, CA (US)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 121 days.

(21) Appl. No.: 15/463,074

(22) Filed: Mar. 20, 2017

(65) Prior Publication Data
US 2018/0267128 A1   Sep. 20, 2018

(51) Int. Cl.
*G01R 31/02* (2006.01)
*G01R 33/60* (2006.01)
(Continued)

(52) U.S. Cl.
CPC ...... *G01R 33/60* (2013.01); *G01R 31/318511* (2013.01); *G01R 33/345* (2013.01);
(Continued)

(58) Field of Classification Search
USPC ................. 324/639, 642, 650, 652
See application file for complete search history.

(56) References Cited

U.S. PATENT DOCUMENTS 7,545,139 B2    6/2009  Saruki et al.
8,959,980 B2    2/2015  Vodnick et al.
(Continued)

FOREIGN PATENT DOCUMENTS

WO    WO 2017/171848    10/2017

OTHER PUBLICATIONS

PCT Search Report, International Application No. PCT/US2018/020361, Applicant: Headway Technologies, Inc., dated Jul. 6, 2018, 21 pgs.
(Continued)

*Primary Examiner* — Vincent Q Nguyen
(74) *Attorney, Agent, or Firm* — Haynes and Boone, LLP (57) ABSTRACT

A ferromagnetic resonance (FMR) measurement system is disclosed with a waveguide transmission line (WGTL) connected at both ends to a mounting plate having an opening through which the WGTL is suspended. While the WGTL bottom surface contacts a portion of magnetic film on a whole wafer, a plurality of microwave frequencies is sequentially transmitted through the WGTL. Simultaneously, a magnetic field is applied to the contacted region thereby causing a FMR condition in the magnetic film. After RF output is transmitted through or reflected from the WGTL to a RF detector and converted to a voltage signal, effective anisotropy field, linewidth, damping coefficient, and/or inhomogeneous broadening are determined based on magnetic field intensity, microwave frequency and voltage output. A plurality of measurements is performed by controllably moving the WGTL or wafer and repeating the simultaneous application of microwave frequencies and magnetic field at additional preprogrammed locations on the magnetic film.

20 Claims, 7 Drawing Sheets

(51) Int. Cl.
*G01R 33/345* (2006.01)
*G01R 31/3185* (2006.01)
*H01P 5/18* (2006.01)
*H01L 43/08* (2006.01)
*H01L 43/10* (2006.01)
*G01N 24/10* (2006.01)
*G01R 33/30* (2006.01)

(52) U.S. Cl.
CPC .............. *G01N 24/10* (2013.01); *G01R 33/30* (2013.01); *H01L 43/08* (2013.01); *H01L 43/10* (2013.01); *H01P 5/18* (2013.01)

(56) References Cited

U.S. PATENT DOCUMENTS

| | | |
|---|---|---|
| 2009/0212769 A1 | 8/2009 | Stoica et al. |
| 2010/0023294 A1 | 1/2010 | Fan et al. |
| 2014/0097841 A1 | 4/2014 | Yang et al. |
| 2018/0033954 A1* | 2/2018 | Aradhya ................ H01L 43/06 |

OTHER PUBLICATIONS

Mircea Dragos et al: "Near-field microwave probe for local ferromagnetic resonance characterization," Applied Physics Letters, AIP Publishing LLC, US, vol. 90, No. 14, Apr. 2, 2007, pp. 142504-1 to 142504-3.

David M Pozar: "Microwave Engineering 4th ed," Dec. 1, 2011, Chapter 3, Transmission Lines and Waveguides, pp. 95, 158, XP055486442.

"Vector network analyzer ferromagnetic resonance of thin films on coplanar waveguides: Comparison of different evaluation methods," by C. Bilzer et al., AIP Journal of Applied Physics 101, 074505 (2007); Apr. 2007, American Institute of Physics, http://dx.doi.org/10.1063/1.2716995, 5 pgs.

"Open-Circuit One-Port Network Analyzer Ferromagnetic Resonance," by C. Bilzer et al., IEEE Transactions on Magnetics, vol. 44, No. 11, Nov. 2008, pp. 3265-3268.

* cited by examiner

SCANNING FERROMAGNETIC RESONANCE (FMR) FOR WAFER-LEVEL CHARACTERIZATION OF MAGNETIC FILMS AND MULTILAYERS

TECHNICAL FIELD

The present disclosure relates to a system for measuring magnetic properties in magnetic films and multilayers, and a method for doing the same, and in particular, to a waveguide transmission line (WGTL) that is mounted on a platform and installed in an electrical probe station to enable fully automated FMR testing across entire wafers without a need to cut the wafers in engineering or product environments.

BACKGROUND

Magnetic thin films and multilayers play a key role in various types of magnetic storage devices such as a magnetic hard disk (HDD) drive, Magnetic Random Access Memory (MRAM), spin torque oscillator (STO), and magnetic domain wall devices. In order to develop and optimize such devices, characterization of magnetic thin film stacks is necessary. A variety of different magnetic characterization techniques must be used to determine all the essential magnetic parameters such as crystalline anisotropy, surface or interface anisotropy, magnetization saturation (Ms), damping constant ($\alpha$), gyromagnetic ratio ($\gamma$), inhomogeneous broadening, resistance x area product (RA), and magnetoresistive ratio (MR).

FMR is a well-established method of measuring anisotropy fields, as well as the gyromagnetic ratio $\gamma$, and the damping constant $\alpha$ of magnetic films and multilayers in extended unpatterned films or in sub-micron patterned structures. The resonance frequency $f_R$ of a ferromagnetic film is given by the so-called Kittel formula shown in equation (1) below where $H_R$ is the resonance field applied perpendicular to the plane of the film, $H_K$ is the effective anisotropy field which includes structural, surface, and magnetostatic contributions, and $\gamma$ is the gyromagnetic ratio.

$$2\pi f_R = \gamma(H_R + H_K) \quad \text{(Eq. 1)}$$

A FMR experiment is performed by probing the magnetic system (thin film, multilayer stack, or structured device) with a combination of microwave excitation and a quasi-static magnetic field. FMR data is obtained by either sweeping the magnetic field at a constant microwave frequency, or by sweeping the frequency at a constant field. When the ferromagnetic resonance condition is achieved, it may be detected by an enhanced absorption of the microwave by the ferromagnetic sample. Thus, resonance (FMR) conditions are defined by pairs of magnetic field and microwave frequency values ($H_R$, $f_R$).

There are several ways of submitting a ferromagnetic sample to microwave excitation. Historically, FMR experimental conditions employed tubular waveguides, and samples were placed in a resonant cavity between poles of an electromagnet. More recently, new methods have been developed that are well suited to analyze film shaped samples. In particular, the wafer under test (WUT) is placed in contact with a non-magnetic waveguide transmission line (WGTL) that may be in the form of a grounded coplanar waveguide (GCPWG), coplanar waveguide (CPWG), co-axial waveguide (CWG), stripline (SL), or a microstrip (MS). The power transmitted or reflected by the WGTL is monitored as a function of the applied magnetic field and microwave frequency.

Figure 1A:
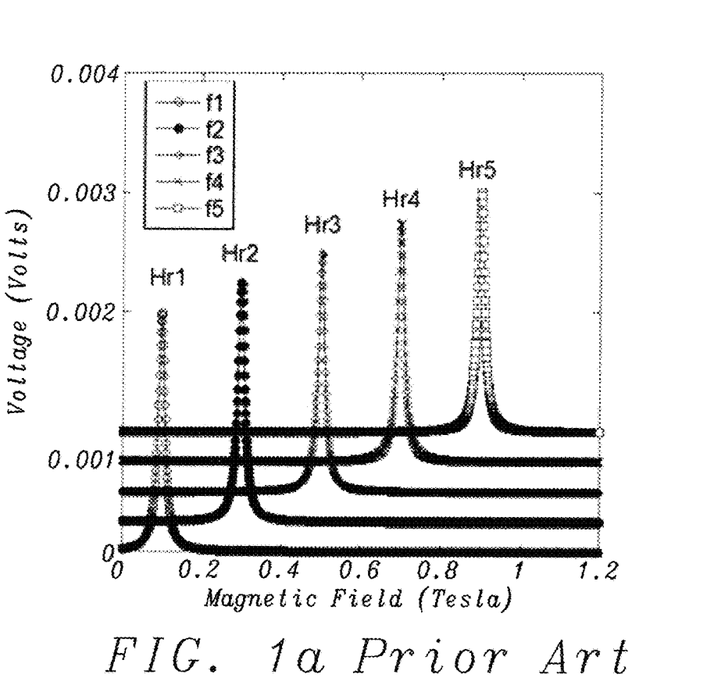
FIG. 1a shows a schematic description of the typical series of Lorentzian shaped peaks derived from ferromagnetic resonance measurements taken for 24 GHz to 48 GHz microwave frequencies.

Referring to FIG. 1a, a schematic depiction is shown where output voltages are plotted as a function of a variable magnetic field at constant microwave frequency using five different values (f1-f5) of microwave frequency. The center and width of the Lorentzian peaks is extracted from the data as a function of the excitation frequency. As mentioned previously, the center field is the resonance field ($H_R$), which is related to the excitation frequency following the Kittel formula that is rewritten in a slightly different form in equation (2) below where h is the Planck constant and $\mu_B$ is the Bohr magneton.

$$H_R(f) = [h/(\gamma \times \mu_B)] \times f - H_K \quad \text{(Eq. 2)}$$

Figure 1B:
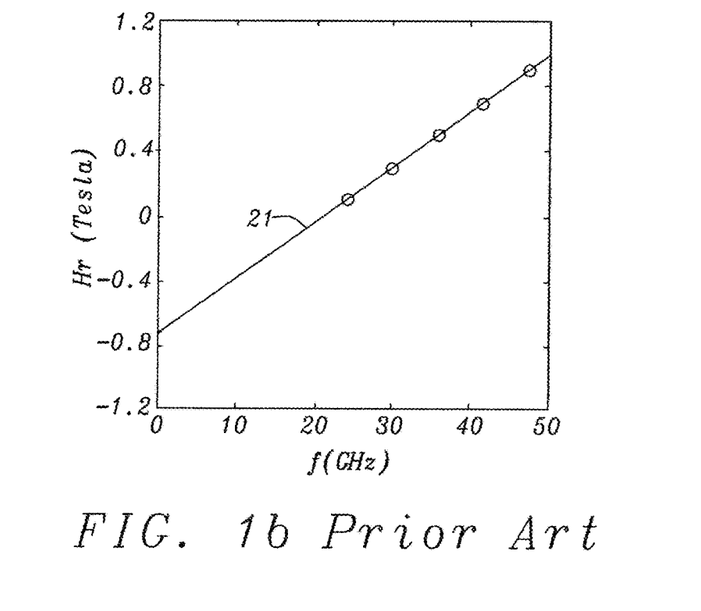

The variation of $H_R$ with microwave frequency is shown in FIG. 1b where each of the points along curve 21 is derived from one of the Lorentzian shaped peaks Hr1-Hr5 in FIG. 1a. As indicated by equation (2), the extrapolation of the data to f=0 gives the value of the effective anisotropy field $H_K$.

The linewidth L of the resonance peak is the width at half amplitude $\Delta H$ of the resonance peak and is related to dissipative processes involved in magnetization dynamics.

The linewidth depends on the excitation frequency and the dimensionless Gilbert damping constant $\alpha$ according to equation (3) below where $L_0$ is an inhomogeneous broadening. By fitting $H_R$ and L with respect to the excitation frequency $f_R$, $H_K$, as well as $\alpha$ and $\gamma$ may be derived.

$$L(f) = (2h\alpha/\gamma \times \mu_B)f + L_0 \quad \text{(Eq. 3)}$$

A network analyzer for detecting FMR in thin CoFe and CoFeB films on a coplanar waveguide is described by C. Bilzer et al. in "Vector network analyzer ferromagnetic resonance of thin films on coplanar waveguides: Comparison of different evaluation methods" in J. of Applied Physics 101, 074505 (2007), and in "Open-Circuit One-Port Network Analyzer Ferromagnetic Resonance" in IEEE Trans. Magn., Vol. 44, No. 11, p. 3265 (2008). In these experiments, the planar WGTL is typically attached to radiofrequency (RF) connectors by microwave electrical probes and placed between the poles of an electromagnet. Thus, given the size of the WGTL (about 5 mm long), and the size of the gap of typical electromagnets, only small size samples (normally <1 inch in diameter) can be measured. Accordingly, wafers typically used in the microelectronics industry (having diameters of 6, 8, 12 inches or more) can only be measured with this FMR technique if they are cut into small coupons.

Figure 2:
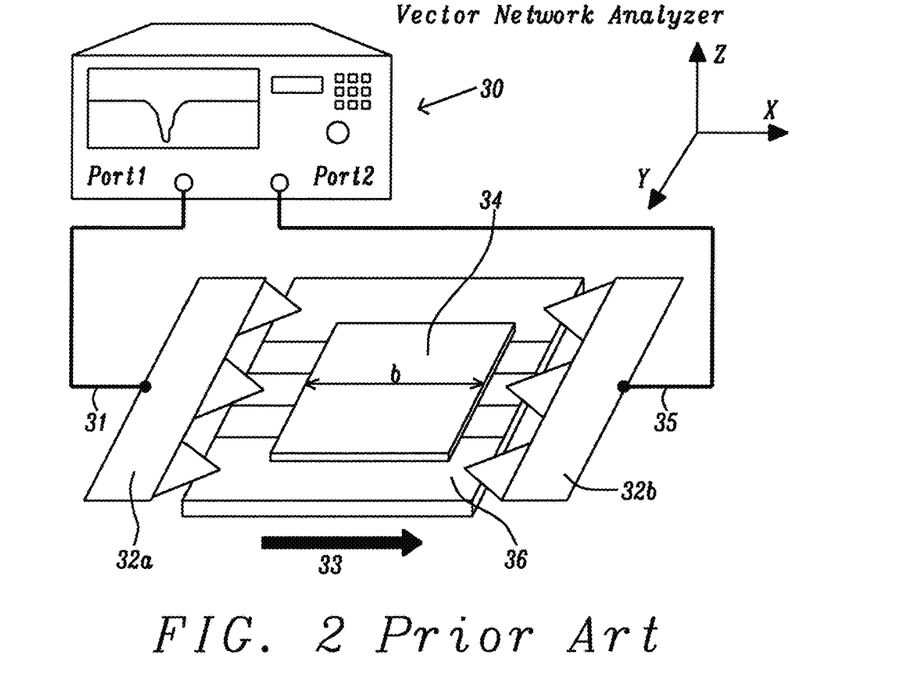
FIG. 2 is a diagram that illustrates a prior art FMR measurement scheme.

FIG. 2 is reproduced from "Microwave susceptibility of thin ferromagnetic films: metrology and insight into magnetization dynamics", Claus Bilzer, Ph.D. report, Universite Paris Sud—Paris XI, 2007) and depicts a conventional FMR system. Vector network analyzer 30 is connected from one port through a first coaxial cable 31 to a first microwave probe portion 32a that is attached to coplanar waveguide (CPWG) 36. A top surface of the CPWG adjoins a magnetic film 34 mounted on a substrate. When a microwave frequency from probe 32a and an external magnetic field 33 are applied in an x-axis direction across the magnetic film, an output signal in a transmission mode passes into a second microwave probe portion 32b and then through a second coaxial cable 35 before returning to the VTA at a second port. Magnetic film size b is typically restricted to 1 inch or less, which means the magnetic film sample 34, must be cut from a whole wafer.

Since conventional FMR techniques are destructive, impractical, and time consuming, they are undesirable to an extent that prevents wide acceptance of FMR as a characterization tool in the magnetic data storage industry. An improved FMR measurement system and technique is needed that enables fully automated FMR measurements on whole wafers for faster throughput, and results in reduced cost by providing a non-invasive test that avoids cutting wafers.

SUMMARY

One objective of the present disclosure is to provide a fully automated system for FMR measurements so that wafer throughput is improved, and wafer destruction associated with wafer cutting to prepare test samples is avoided.

A second objective of the present disclosure is to provide a fully automated system according to the first objective that includes a waveguide transmission line (WGTL) for performing the FMR test with the capability to characterize a plurality of sites on magnetic thin films and multilayers formed on unpatterned or patterned whole wafers.

These objectives are achieved according to one embodiment of the present disclosure with a FMR test system that is configured around a controller (computer) linked to an electrical probe station comprising a WGTL connected on one end to a RF generator and on the other end to a RF power detector (diode), a magnetic field pole positioned above the WGTL, and a wafer chuck that holds a wafer under test (WUT) under the WGTL and moves laterally in a preprogrammed direction with respect to the WGTL. A RF input cable from the RF generator is attached to a first end launch RF connector, which is connected to a first end of the WGTL and provides a RF input signal thereto. The WGTL is connected at a second end to a second end launch RF connector that is attached to a RF output cable. Both end launch RF connectors are rigidly clamped to a mounting plate, and at least a portion of the WGTL protrudes through and below an opening in the mounting plate.

According to one FMR measurement mode disclosed herein, the controller directs the wafer chuck and WUT to move in an x-axis and/or y-axis direction parallel to the plane of the mounting plate such that the WGTL is aligned above a predetermined (x, y) coordinate on the WUT. The WGTL is separated from the WUT by a gap distance in the z-axis direction thereby avoiding contact. Then, the WUT is moved in a vertical direction to establish contact between a WGTL bottom surface and a top surface of a magnetic film on the WUT. In other embodiments, the WUT is held stationary while the mounting plate and WGTL are moved above a series of predetermined (x, y) coordinates on the WUT. At certain x-axis and y-axis coordinates that are pre-programmed into the controller, the WGTL is vertically moved to contact the magnetic film top surface. In some embodiments, the WGTL has a substantially U-shape while in other embodiments, the WGTL has planar top and bottom surfaces.

While the WGTL makes contact with a portion of the magnetic film top surface, a static magnetic field is applied from a magnetic pole piece that is positioned above the opening in the mounting plate and directly above the WGTL contact area. The WGTL transmits a sequence of microwave frequencies (RF input signals) to the wafer. A FMR condition is established in the magnetic film with each applied microwave frequency, and the extent of microwave absorption by the magnetic film is dependent on the magnitudes of the microwave frequency, static magnetic field, and magnetic properties of the thin magnetic film.

As a result of FMR absorption by the magnetic film, there is a power loss between the first and second ends of the WGTL that is detected by the RF power diode. The RF power diode also known as the RF detector converts each RF output signal from the WGTL to a voltage readout that the controller uses to calculate Hk, and $\alpha$, for example, for the magnetic film. After each FMR measurement, the wafer chuck and WUT are lowered to a gap distance k>0, and then moved to the next (x, y) coordinate for a subsequent FMR measurement. Thus, the FMR measurement sequence comprises a "step and repeat" pattern in which the chuck and WUT are moved laterally (stepped) to align the WGTL above a new (x, y) coordinate on the WUT, raised to make contact with the WGTL, and then lowered to the gap distance after the measurement. The area of the contacted region on the magnetic film is sufficiently large to detect Hk and $\alpha$ for a plurality of thousands of magnetic storage devices within the contacted region.

According to one embodiment, a commercial WGTL with a flat, rectangular shape is modified to provide sufficient flexibility that enables the WGTL to be bent without breakage.

The present disclosure also encompasses an embodiment where the RF input and output cables are attached to first and second end launch RF connectors, respectively, which in turn are affixed to a top surface of a flat WGTL. The WGTL bottom surface is below the mounting plate and is unencumbered when contacting a magnetic film top surface during a FMR measurement. Preferably, the end launch RF connectors should not extend below the plane of contact between the WGTL and magnetic film to allow contact or close proximity between the WGTL and WUT.

Since a single controller may be employed to manage all aspects of the testing including wafer chuck and mounting plate movement, RF signal processing, magnetic field generation, and compilation of the test data, throughput is optimized so that the system and FMR measurement method may be readily implemented in an engineering or production environment.

BRIEF DESCRIPTION OF THE DRAWINGS

FIG. 1b shows a plot of resonance field ($H_R$) as a function of the microwave frequencies used in FIG. 1a.

FIG. 11b is a plot of $H_K$ vs. thickness taken from data obtained during the FMR measurements used to generate FIG. 11a.

DETAILED DESCRIPTION

The present disclosure is a scanning FMR system that is designed to measure magnetic properties including $H_K$ and a for magnetic films or multilayers on a whole wafer at a plurality of locations identified by their (x, y) coordinates. The scanning FMR system is fully automated and features a mounting plate with a center opening in which a waveguide transmission line (WGTL) is suspended from two ends that are attached to RF connectors rigidly held on a mounting plate. It should be understood that the term "RF connector" encompasses various types of RF connectors including end launch RF connectors mentioned in the exemplary embodiments. However, other embodiments may comprise other types of RF connectors used in the art but not described herein. X-axis and y-axis coordinates on the wafer under test (WUT) are in a plane that is aligned parallel to and below the plane of the mounting plate. Each FMR measurement site on a magnetic film has a pair of coordinates $(x_n, y_n)$ where n is an integer. The z-axis direction in the drawings is orthogonal to the plane of the WUT. The present disclosure also encompasses a FMR test method for measuring magnetic properties of one or more films on patterned or unpatterned wafers.

Figure 3:
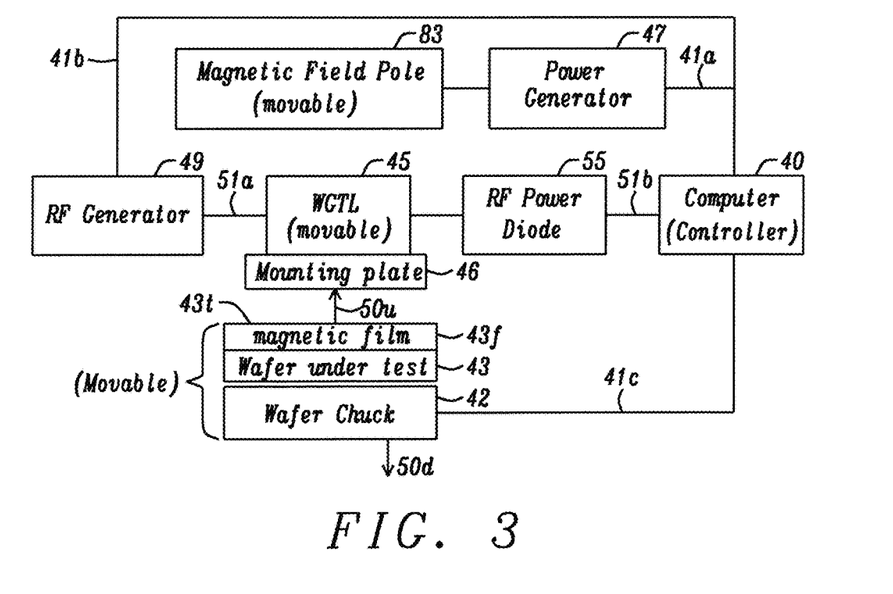
FIG. 3 is a diagram showing the various components of a fully automated FMR measurement system according to a first embodiment of the present disclosure that represents a transmission mode for performing FMR measurements.

Referring to FIG. 3, one embodiment of a FMR measurement system according to the present disclosure is depicted in a diagram that shows the layout of the major components. There is a computer hereafter called the controller 40 to manage the movement of the WGTL 45 and the mounting plate 46 to which the WGTL is affixed. The magnetic field pole 83 may also be moved by the controller to maintain a position above the WGTL and the test location of a magnetic film 43f on the WUT 43 as explained later. It should be understood that the term "magnetic film" may comprise one or a plurality of magnetic films formed in a stack of layers. In some embodiments, the WUT is held on a top surface of a wafer chuck 42 by a vacuum, and the wafer chuck and WUT are moved in a programmed manner while the magnetic field pole, WGTL, and mounting plate are maintained in a stationary position. In preferred embodiments, a magnetic field is applied to a predetermined $(x_n, y_n)$ coordinate on the WUT while a signal path layer of the WGTL contacts a top surface 43t of the magnetic film at the $(x_n, y_n)$ coordinate. As a result of simultaneously applying a microwave frequency by the WGTL and magnetic field of up to 3 Tesla from the magnetic pole piece, a ferromagnetic resonance (FMR) condition is established in the magnetic film proximate to the predetermined (x, y) coordinate on the WUT. The WGTL may be a microstrip, grounded coplanar waveguide, coplanar waveguide, stripline, or coaxial waveguide.

The RE detector may be a power diode 55 that detects a RF output signal from the WGTL corresponding to a RF power loss caused by the FMR condition where a certain amount of microwave power is absorbed and excites the magnetic film to a resonance state. After the FMR measurement is performed at the $(x_n, y_n)$ coordinate, the wafer chuck and WUT are lowered 50d via a signal through link 41c to reestablish a gap below the WGTL. Subsequently, the wafer chuck and WUT are moved to another predetermined $(x_n, y_n)$ coordinate and the chuck is raised 50u to enable the WGTL to contact magnetic film top surface 43t for another FMR measurement.

The controller 40 has a first link 41a to a power generator 47 that is responsible for providing an appropriate magnetic field from the magnetic field pole 83 so that an applied microwave frequency and the applied field induce a FMR condition in the magnetic film 43f when the probe chuck 42 and WUT 43 are raised 50u to enable contact of the magnetic film with a WGTL bottom surface (not shown) that is suspended through and below an opening in the mounting plate 46. Meanwhile, the controller has a second link 41b to a RF generator 49 that provides a plurality of microwave frequencies through RF input cable 51a to one end of the WGTL.

In a preferred operating mode, the applied magnetic field is varied (swept from a minimum to a maximum value) at constant microwave frequency. The FMR measurement may be repeated for a plurality of different microwave frequencies. The RF power diode converts the power output to a voltage signal that is transmitted through an output cable 51b to the controller. Thereafter, the controller calculates $H_k$ and a based on each pair of applied magnetic field value and applied microwave frequency used to establish a FMR condition, and on voltage output data from the RF power diode for each $(x_n, y_n)$ coordinate used in the FMR measurement sequence.

The present disclosure anticipates that layouts other than the one illustrated in FIG. 3 may be employed to generate the microwave excitation (FMR condition) of a magnetic film sample, and detect the absorption therein. For instance, a vector network analyzer (VNA) similar to the VNA 30 depicted in FIG. 2 may be used as a RF output generator and RF input analyzer. In another embodiment related to pulsed inductive microwave magnetometry (PIMM), a pulse generator and a time-resolved oscilloscope may serve as a RF source and RF analyzer, respectively. In yet another embodiment, a lock-in amplifier detection technique known to those skilled in the art may be employed to amplify the FMR output signal (power loss).

Figure 4:
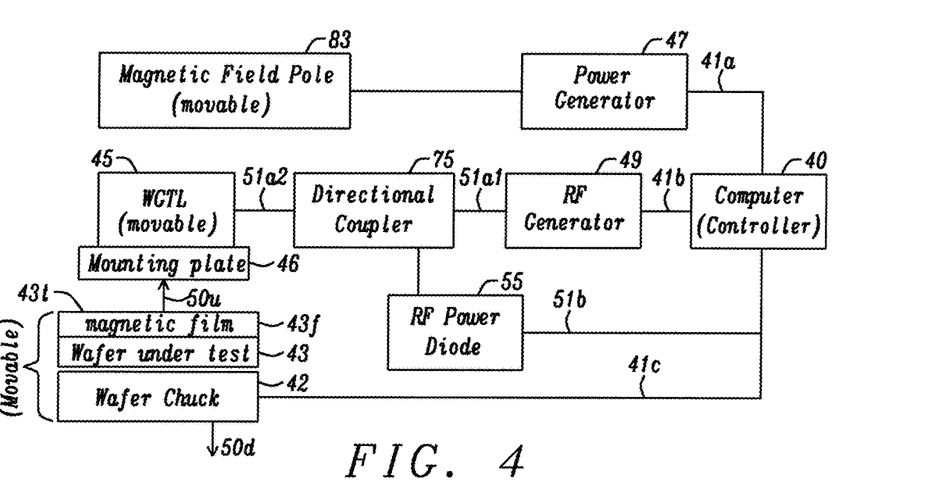
FIG. 4 is a diagram showing the various components of a fully automated FMR measurement system according to a second embodiment of the present disclosure that represents a reflective mode for performing FMR measurements.
Figure 5:
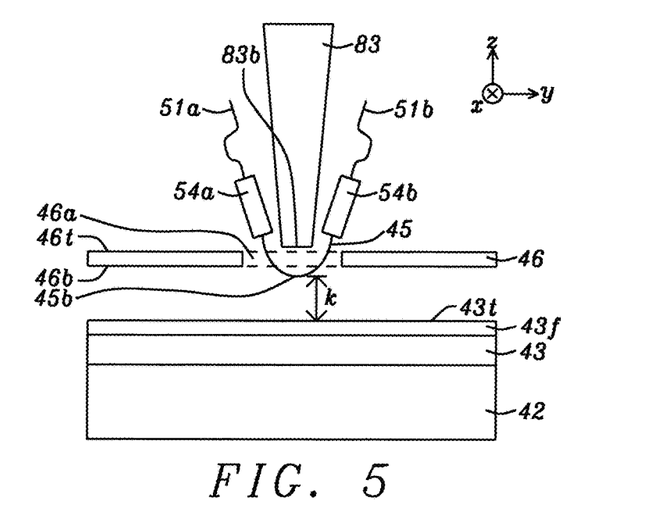
FIG. 5 is cross-sectional view of a FMR measurement system according to the present disclosure wherein a bent WGTL is attached to a mounting plate, and the wafer under test is held on a movable chuck during FMR measurements.
Figure 6:
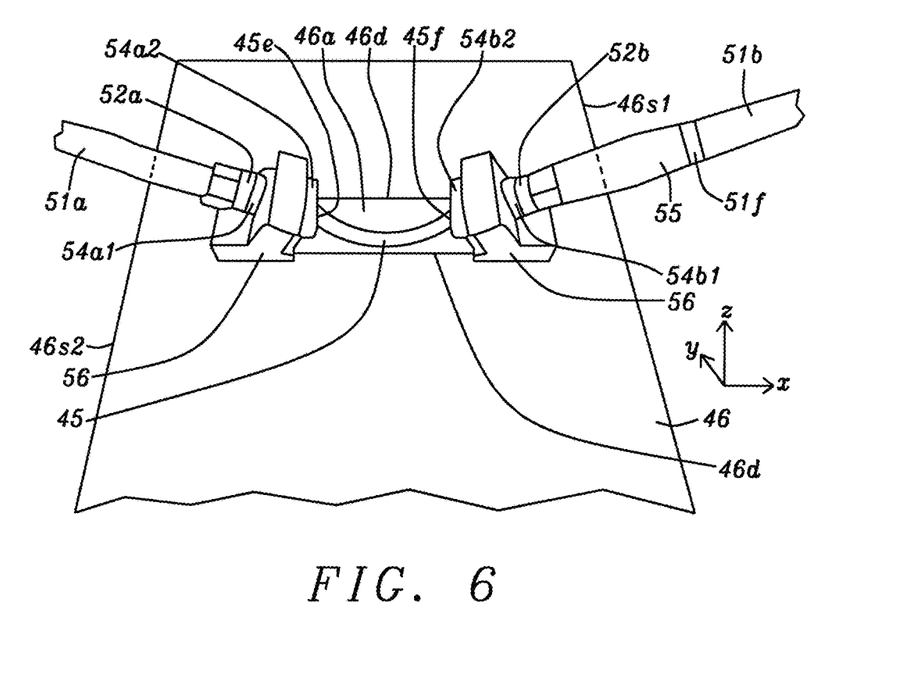
FIG. 6 is an oblique view of the embodiment in FIG. 5 where the bent WGTL is suspended over an opening in a mounting plate, and a middle portion of the WGTL is below the plane of the mounting plate.

According to various embodiments of the present disclosure, FMR measurements are performed by analyzing a RF signal transmitted through a WGTL as described with respect to FIG. 3 and FIGS. 5-6, or by measuring a RF signal that is reflected from a waveguide terminated by an open-circuit or short-circuit. An embodiment showing a reflectance mode of operation is depicted in FIG. 4 where a directional coupler 75 is inserted between the RF generator 49 and WGTL 45 to transmit a RF input signal to the WGTL and receive a RF output signal reflected from the WGTL. Alternatively, a power divider or a bias tee may be used instead of the directional coupler as appreciated by those skilled in the art. Microwave frequencies are inputted from the RF generator through a first input cable 51a1 to the directional coupler and then through a second input cable 51a2 to the WGTL. All other components of the transmission mode layout in FIG. 3 are retained.

In some embodiments, the RF input and output signals pass through an end launch RF connector (not shown) positioned between the second input cable and the WGTL. In particular, the directional coupler receives reflected RF signals (output signals) from the WGTL through cable 51a2 and then directs the signals to the RF power diode 55 where a conversion occurs to a voltage output signal for each pair of applied magnetic field and applied microwave frequency ($H_R$, $f_R$) as previously described. The output signal is then transmitted to the controller 40 through output cable 51b.

Referring to FIG. 5, a cross-sectional view of a FMR measurement system based on RF signal transmission through a WGTL is shown according to a first embodiment of the present disclosure, and includes the magnetic pole piece 83, bent WGTL 45, and magnetic film 43f on WUT 43. In the exemplary embodiment, the WGTL has a first end attached to an end launch RF input connector 54a and a second end connected to an end launch RF output connector 54b such that both end launch RF input/output connectors are above a top surface 46t of mounting plate 46. The WGTL is bent in a substantially U-shape and protrudes through opening 46a such that a middle portion 45b hereafter called the tip portion is below a bottom surface 46b of the mounting plate. According to one embodiment, the mounting plate along with the WGTL and WUT are installed on a commercial electrical probe station that is available from different vendors.

During intervals when no FMR measurements are being performed, the tip portion 45b is a gap distance k>0 from the top surface 43t of magnetic film 43f on WUT 43. As indicated previously, when the FMR system is programmed to perform a FMR measurement at a certain ($x_n$, $y_n$) coordinate, the wafer chuck is raised so that k=0 until the FMR measurement is completed. In an alternative embodiment, k is proximate to 0 and sufficiently small, preferably less than 100 micrometers, to enable efficient transmission of microwaves from the WGTL to the magnetic film. It is important that the magnetic pole tip 83b is above opening 46a and aligned over the ($x_n$, $y_n$) coordinate where tip portion 45b makes contact with top surface 43t so that the same region proximate to the ($x_n$, $y_n$) coordinate is exposed to both of the magnetic field and microwave frequency.

Referring to FIG. 6, an oblique view of the mounting plate 46 and WGTL 45 in FIG. 5 is depicted with the magnetic pole piece removed. According to one embodiment, opening 46a has two parallel sides 46d that are aligned in an x-axis direction and may be substantially orthogonal to mounting plate sides 46s1, 46s2. At each end of opening 46a where sides 46d terminate, there is an end launch RF connector. One "outer" end 54a1 of a first end launch RF connector is attached to RF input connector 52a and a second "inner" end 54a2 is connected to end 45e of the WGTL. Meanwhile, an inner end 54b2 of a second end launch RF connector is attached to end 45f of the WGTL, and an outer end 54b1 thereof is attached to RF output connector 52b. Thus, microwave frequencies in the range of 1-100 GHz are sent from the RF generator (not shown) through input cable 51a to the WGTL via the first end launch RF connector, and output RF signals are transmitted via the second end launch RF connector to RF diode 55. According to one embodiment, WGTL 45 is bent in order to be compatible with suspension through opening 46a in the mounting plate design, and to provide a small contact area (plurality of square millimeters) with the magnetic film on the underlying WUT.

The entire WGTL assembly (WGTL and end launch RF connectors) is affixed to the mounting plate 46 by two removable and retractile clamps 56. Opening 46a may be formed therein by a conventional method and has an x-axis dimension of sufficient length to enable a bent WGTL to be suspended between the two clamps, and have a middle tip portion below the plane of the mounting plate.

The present disclosure also encompasses a second embodiment of an FMR measurement system similar to the scheme depicted in FIG. 6 except the WGTL is not bent and has planar top and bottom surfaces. To enable a bottom surface of a flat WGTL to make contact with a magnetic film beneath opening 46a in the mounting plate, a different end launch RF connector is required.

Figure 7A:
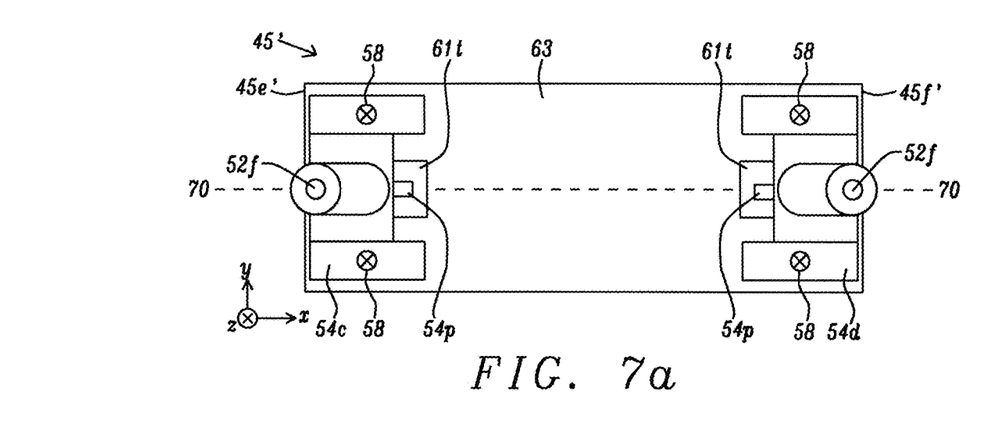
FIG. 7a and FIG. 7b are a top view, and cross-sectional view, respectively, of a flat WGTL with backside end launch RF connector attachments according to another embodiment of the present disclosure.

Referring to the top view of the second embodiment in FIG. 7a, a key feature in addition to the flat WGTL 45' is a second type of end launch connector 54c, 54d which is affixed to a top surface of a rigid substrate 63 proximate to ends 45e', 45f', respectively, of the flat WGTL by bolts 58. A RF input cable (not shown) is connected to the RF connector 52f of the end launch connector 54c proximate to end 45e', and a RF power diode (not shown) is connected to the RF connector 52f of the end launch connector 54d proximate to end 45f'. Each end launch connector has a pin 54p at an inner side that contacts a top conductor layer 61t. The bolts preferably extend through an opening (not shown) into the rigid substrate to securely hold the WGTL, especially during lateral movements in the (x, y) plane and vertical movements in a z-axis direction that are required for FMR measurements. Plane 70-70 is aligned along the x-axis direction and bisects the flat WGTL.

Figure 7B:
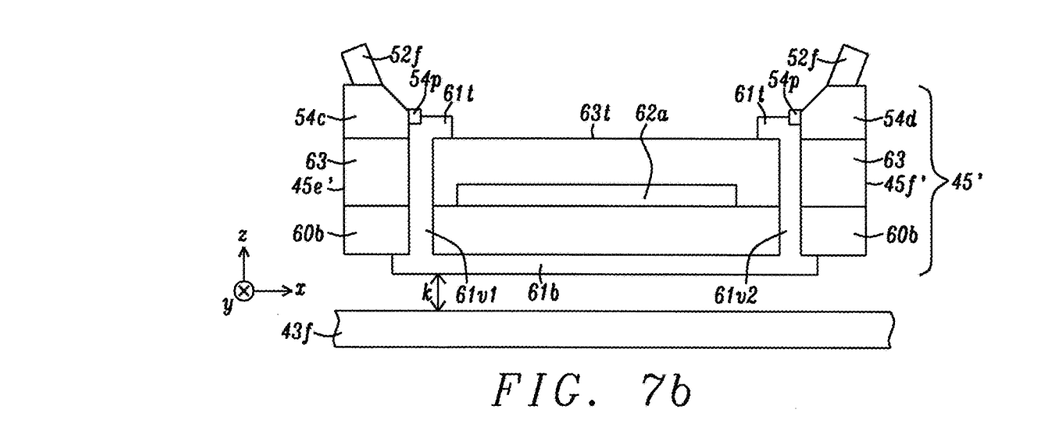

FIG. 7b depicts a cross-sectional view of the flat WGTL 45' and end launch connectors at plane 70-70 in FIG. 7a. As a result of affixing the end launch connectors 54c and 54d to a top surface 63t of the rigid substrate that is an upper layer in the WGTL, the bottom surface that comprises signal path layer 61b is clear to make contact with an underlying magnetic film 43f during a FMR measurement. According to one embodiment, at least a bottom portion of the flat WGTL including the signal path layer is suspended through an opening in the mounting plate. Alternatively, the flat WGTL may be suspended below the opening. Dielectric layer 60b separates the signal path layer from rigid substrate 63 and top ground path layer 62a. Gap k is shown during a stationary position between FMR measurements when there is no contact between the WGTL and magnetic film. Top conductor layer 61t is connected to the signal path layer by a first via 61v1 that may be positioned below a first pin 54p at end launch connector 54c, and by a second via 61v2 that may be positioned below the second pin 54p at end launch connector 54d. Ground path and signal path layers are typically made of a conductive metal.

During a FMR measurement when a magnetic field is applied to an area around an (x, y) coordinate of the magnetic film contacted by the WGTL, a microwave frequency passes through end launch connector 54c and the top conductor layer 61t, and then through via 61v1 and into the signal path layer 61b. A portion of the microwave power is absorbed by the magnetic film 43f during a FMR condition so that the output RF signal carried through via 61v2 and out through end launch connector 54d has reduced power compared with the input RF signal. The RF power diode (not shown) converts the output RF power signal for each ($H_R$, $f_R$) pair to a voltage measurement that is relayed to the controller.

Figure 8:
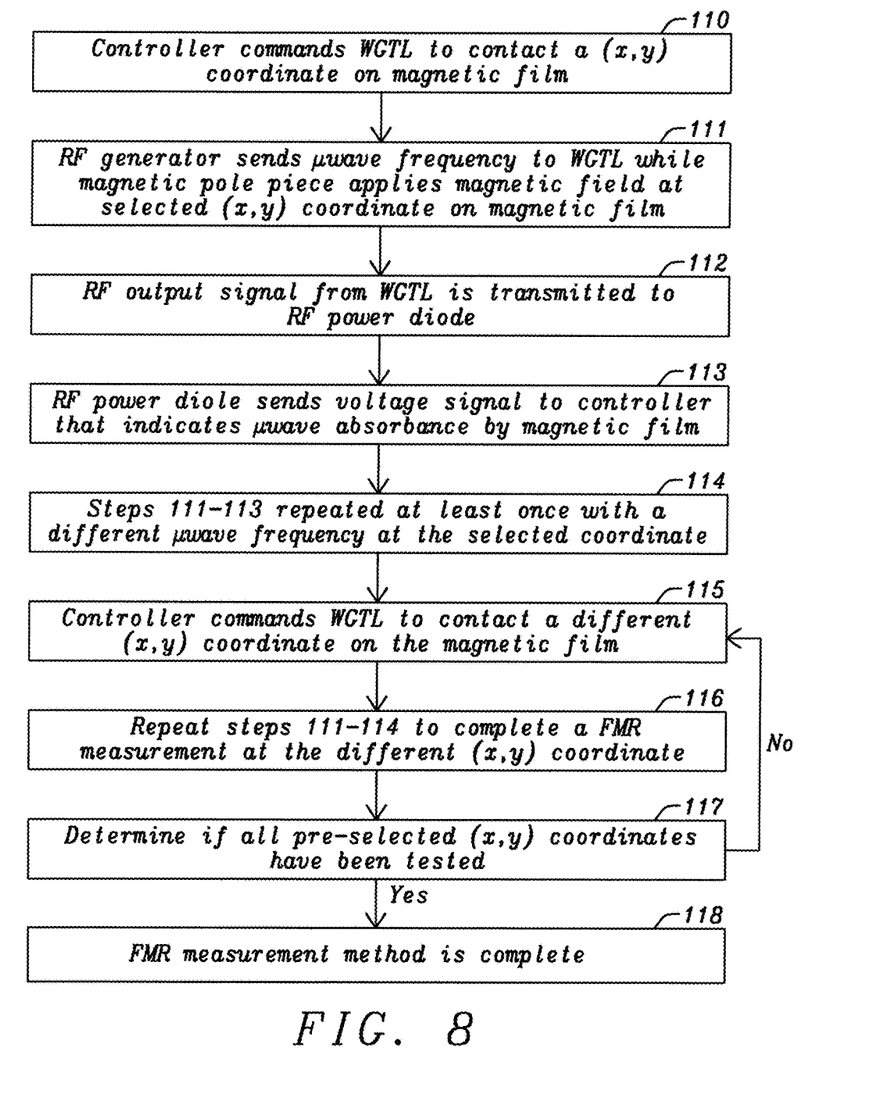
FIG. 8 is a flow diagram showing various steps of performing a FMR measurement according to a method of the present disclosure.

Referring to FIG. 8, a FMR measurement method is illustrated in a flow diagram according an embodiment of the present disclosure, and may be employed for both of the embodiments relating to a bent WGTL or flat WGTL. In step 110, the controller (described earlier with regard to a transmission mode in FIG. 3 or a reflectance mode in FIG. 4) commands a WGTL through link 41c, for example, to contact a first location that is represented by a (x, y) coordinate on a magnetic film to be tested. Contact is achieved by lowering the WGTL and mounting plate, or by raising the wafer chuck and overlying wafer under test with an exposed top surface of the magnetic film (see movement 50u in FIGS. 3, 4). Next, in step 111, the controller through another link 41b instructs a RF generator to send a microwave frequency F1 to the WGTL while an overlying magnetic pole piece applies a magnetic field at the selected (x, y) coordinate.

As a result of the simultaneous application of microwave frequency F1 and the magnetic field, the magnetic film achieves a FMR condition and absorbs a portion of the microwave power that depends on the magnetic properties of the magnetic film, F1, and the applied field ($H_R$). Accordingly, in step 112, the RF power diode detects a reduced power value in the RF output signal compared with the value specified by the controller in the RF input signal from step 111.

In step 113, the RF power diode converts the RF output signal to a voltage measurement that is transmitted to the controller and indicates the microwave absorbance by the magnetic film for applied microwave frequency F1 and applied magnetic field $H_R$.

Step 114 comprises a repetition of steps 111-113 except the RF input signal has a second frequency F2 that is applied to the magnetic film at the previously selected (x, y) coordinate after F1 is applied. In some embodiments, steps 111-113 are repeated a plurality of times at each (x, y) coordinate used for the FMR measurement method. In other words, a third frequency F3 that differs from F1 and F2 may be applied during an interval of time after F2, and so forth up to an "nth" frequency Fn after F3 is applied. Note that the applied magnetic field is swept between a minimum and a maximum value when each frequency F1 up to Fn is applied according to a preferred embodiment. Thus, a FMR condition occurs with each applied frequency, and each FMR condition has a unique microwave absorbance that is translated into a corresponding voltage signal by the RF power diode. In an alternative embodiment, the applied magnetic field is held constant while the microwave frequencies are varied (swept) from F1 up to Fn to establish a FMR condition.

Referring to step 115, the controller commands the wafer chuck and overlying magnetic film to be lowered (movement 50d in FIG. 3) thereby disengaging the WGTL from making contact with the first location. Then, in an embodiment where the wafer chuck and wafer make all the movements in the x-axis and y-axis directions, the controller directs the wafer chuck to move to a second location where the WGTL tip portion is aligned above a different (x, y) coordinate from the initial (x, y) coordinate. The wafer chuck and the magnetic film on the WUT are raised to again make contact with the WGTL.

Thereafter, steps 111-114 are repeated to complete a FMR measurement at the second location. Note that each location may comprise a contact area of a plurality of square millimeters, and each (x, y) coordinate may be a center point in the area contacted by the WGTL.

Depending on the size of the magnetic film area to be contacted by the WGTL, and the number of different positions desired for an FMR measurement, step 116 indicates that steps 111-115 may be repeated a plurality of times to yield a plurality of FMR measurements involving "m" different (x, y) coordinates each with a plurality of ($H_R$, $f_R$) pairs where $f_R$ is one of F1 up to Fn. At step 117, a decision is made whether or not all of the pre-selected (x, y) coordinates on the magnetic film have been tested. If "no", another FMR measurement is taken at a different (x, y) coordinate. If "yes", step 118 indicates the FMR measurement process is complete.

As mentioned earlier, the controller is capable of determining magnetic properties in the magnetic film at each location corresponding to a different (x, y) coordinate. Each FMR measurement yields one or more pairs (frequency, field) also referred to as ($H_R$, $f_R$) pairs in equation (1) corresponding to each FMR condition. The controller uses FMR measurement data and one or more of equations (1)-(3) described previously to determine Hk, α, and in some cases γ and inhomogeneous broadening ($L_0$).

An experiment was performed using the FMR system with a bent WGTL shown in FIGS. 5-6 and demonstrates how effective perpendicular magnetic anisotropy field (Hk) is monitored across an unpatterned film comprised of a stack of magnetic tunnel junction (MTJ) layers. In this example, 43 regions each having a different (x, y) coordinate on an uncut 8-inch diameter wafer were tested by applying microwave frequencies between 10-40 GHz and magnetic fields up to 1 Tesla (10000 Oe) according to a FMR measurement method of the present disclosure. Each region has a rectangular shape with a length of about 10 mm along the x-axis direction, and a width of about 9 mm in the y-axis direction. The FMR measurement at each (x, y) coordinate required about two minutes of process time for a total FMR measurement time of around 90 minutes for the entire wafer.

Figure 9:
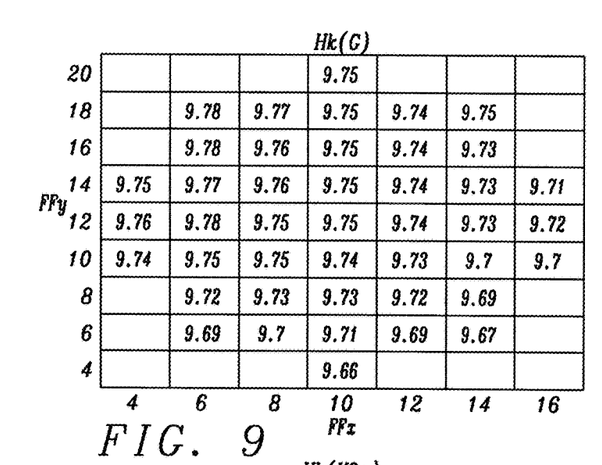
FIG. 9 shows the FMR measurement results of $H_K$ as a function of x-axis and y-axis coordinates of a perpendicular magnetic tunnel junction (pMTJ) stack with a nominal uniform thickness across the entire wafer, and obtained according to a method described herein.
Figure 10:
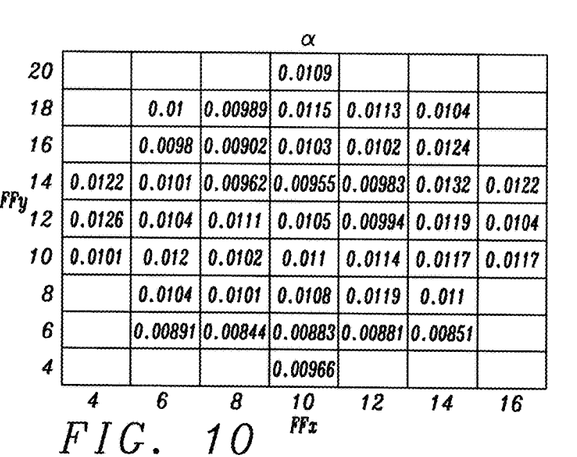
FIG. 10 illustrates FMR measurement results for damping parameter α as a function of x-axis and y-axis coordinates of a pMTJ stack with a nominal uniform thickness across the entire wafer, and obtained according to a method of the present disclosure.

FIG. 9 shows a map of the $H_K$ results and FIG. 10 illustrates a map of the damping coefficient α result for each of the 43 regions on the 8-inch wafer as a function of their x-axis and y-axis coordinates. $H_K$ varies from 9760 Oe in the upper left to 9670 Oe in the lower right corner of the wafer. The MTJ stack used for this experiment was a CoFeB/MgO/CoFeB based MTJ structure. Results show that the MTJ stack has a very high perpendicular magnetic anisotropy (PMA), and a substantially uniform thickness across the wafer.

Figure 11A:
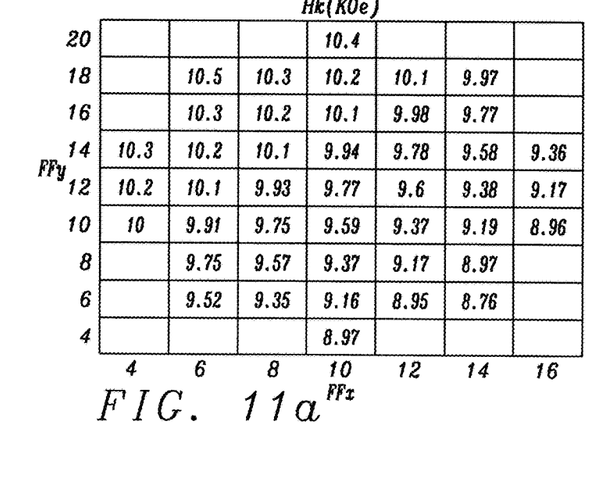
FIG. 11a depicts the FMR measurement results of $H_K$ as a function of x-axis and y-axis coordinates for a magnetic thin film with a variable thickness on a wafer according to an embodiment of the present disclosure.
Figure 11B:
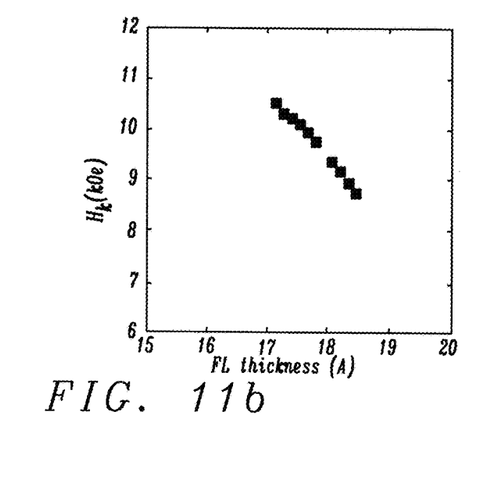

In a second experiment, the same MTJ stack of layers was retained from the first experiment. However, the free layer thickness was purposely varied from 17 Angstroms in the upper left portion of the wafer by small increments to 18.5 Angstroms in the lower right corner to demonstrate how the FMR measurement system and method of the present disclosure may be advantageously used as a tool to explore $H_K$ dependence on free layer thickness. The experimental results are mapped in FIG. 11a and show how $H_K$ varies from 10500 Oe in the upper left portion of the wafer to 8760 Oe in the lower right corner of the wafer. FIG. 11b shows the results of $H_K$ as a function of thickness along the plane 95-95 in FIG. 11a. In particular, a substantially linear plot is formed which indicates $H_K$ steadily increases as the free layer thickness is gradually reduced from 18.5 Angstroms to 17 Angstroms.

RF connectors, the probe station (platform), RF generator, RF power diode, input and output cables, as well as alternative RF devices such as vector network analyzers, pulse generators, and time-resolved oscilloscopes are commercially available. A suitable magnet comprising a magnetic pole piece that delivers the required magnetic field to induce a magnetic resonance according to the present disclosure is also commercially available or may be custom built by one skilled in the art.

While this disclosure has been particularly shown and described with reference to, the preferred embodiment thereof, it will be understood by those skilled in the art that various changes in form and details may be made without departing from the spirit and scope of this disclosure.

We claim:

1. A scanning ferromagnetic resonance (FMR) measurement system, comprising:
    a controller with a first link to a RF generator, a second link to a power generator that is connected to a magnet, and a third link to one or both of a mounting plate on which a bent waveguide transmission line (WGTL) is mounted, and a wafer chuck configured to hold an overlying whole wafer under test (WUT) having a magnetic film with an exposed upper surface, the mounting plate and/or wafer chuck are programmed to move laterally and vertically in a step and repeat fashion, wherein:
    the RF generator is configured to provide a sequence of RF input signals each comprising a different microwave frequency through a RF input cable to the bent WGTL;
    the bent WGTL has a middle tip portion which is configured to contact a predetermined region of the exposed upper surface of the magnetic film during a FMR measurement to sequentially transmit the different microwave frequencies thereto; and
    the magnet comprises a magnetic pole piece aligned above the bent WGTL middle tip portion and providing a magnetic field through a mounting plate opening on the predetermined region of the magnetic film such that a FMR condition is established in the predetermined region thereby causing a unique microwave absorbance for each different microwave frequency that results in a RF power loss for each combination of microwave absorbance and microwave frequency and is detected from a RF output signal that passes from the WGTL to a RF detector, wherein the RF detector is configured to send a voltage signal as an FMR measurement to the controller such that one or more magnetic properties are determined for the magnetic film.

2. The scanning FMR measurement system of claim 1, wherein the bent WGTL and mounting plate are installed in an electrical probe station.

3. The scanning FMR measurement system of claim 1, further comprising a first RF connector that connects the RF input cable to the bent WGTL, and a second RF connector that connects the bent WGTL to the RF detector, wherein the first and second RF connectors do not contact the exposed top surface of the magnetic film or extend beyond a plane of contact between the bent WGTL and the magnetic film.

4. The scanning FMR measurement system of claim 3, further comprising a transmission mode for performing the FMR measurement wherein the RF input signal is transmitted through the first RF connector and the RF output signal is transmitted through the second RF connector.

5. The scanning FMR measurement system of claim 3, wherein the first and second RF connectors are end launch RF connectors.

6. The scanning FMR measurement system of claim 1, further comprising a directional coupler, power divider, or bias tee that receives the RF input signal from the RF generator and then transmits the RF input signal through the RF input cable to the WGTL, wherein the directional coupler, power divider, or bias tee also receives a reflected RF output signal from the WGTL and transmits the reflected RF output signal to the RF detector in a reflectance mode for performing the FMR measurement.

7. The scanning FMR measurement system of claim 1, wherein the bent WGTL has a substantially U-shape.

8. The scanning FMR measurement system of claim 1, wherein the mounting plate and bent WGTL are moved with respect to the WUT and magnetic film, which are held stationary.

9. The scanning FMR measurement system of claim 1, wherein the WUT and magnetic film are moved with respect to the WGTL and mounting plate, which are held stationary.

10. The scanning FMR measurement system of claim 1, wherein the bent WGTL and magnetic film are separated after the FMR measurement by a vertical movement to establish a gap therebetween before a lateral movement is performed to align the bent WGTL over another predetermined region in the magnetic film.

11. The scanning FMR measurement system of claim 1, wherein the FMR condition is established with each of the different microwave frequencies by sweeping the magnetic field from a minimum value to a maximum value.

12. The scanning FMR measurement system of claim 1, wherein the FMR condition is established by holding the magnetic field constant and sweeping with a plurality of different microwave frequencies applied in a sequential order.

13. A scanning ferromagnetic resonance (FMR) measurement system, comprising:
    a mounting plate comprising an opening extending through the mounting plate;
    a bent waveguide transmission line (WGTL) comprising a first end and a second end mounted to a first major surface of the mounting plate, the bent WGTL further comprising an interconnecting portion joining the first end to the second end, wherein the interconnecting portion extends through the opening of the mounting plate;
    a magnetic pole piece arranged over the first major surface of the mounting plate and over a tip of the interconnecting portion of the bent WGTL, the magnetic pole piece being configured to generate a magnetic field;
    a wafer chuck disposed below the mounting plate, wherein a second major surface of the mounting plate is directed toward the wafer chuck;
    a radio frequency (RF) generator configured to provide an RF signal to the bent WGTL, wherein the RF signal in the bent WGTL and the magnetic field generated by the magnetic pole piece are configured to interact with a magnetic film disposed over the wafer chuck; and
    a controller configured to move at least one of the wafer chuck or the mounting plate through a sequence of positions, each position corresponding to a plurality of measurements indicative of the interaction of the RF signal in the bent WGTL and the magnetic field generated by the magnetic pole piece with the magnetic film.

14. The scanning FMR measurement system of claim 13, further comprising:
a first RF connector mounted to the first major surface of the mounting plate and attached to the first end of the bent WGTL; and
a second RF connector mounted to the first major surface of the mounting plate and attached to the second end of the bent WGTL.

15. The scanning FMR measurement system of claim 14, wherein the first end of the bent WGTL comprises an input end of the bent WGTL configured to receive the RF signal, and wherein the second end of the bent WGTL comprises an output end of the bent WGTL configured to output a resultant RF signal indicative of the interaction of the RF signal in the bent WGTL and the magnetic field generated by the magnetic pole piece with the magnetic film, and wherein the scanning FMR measurement system further comprises an RF power measurement device configured to measure the resultant RF signal.

16. The scanning FMR measurement system of claim 15, wherein the RF power measurement device comprises an RF power diode.

17. The scanning FMR measurement system of claim 13, wherein the magnetic field is less than or equal to 3 Tesla, and wherein the RF signal comprises a plurality of different microwave frequencies ranging from 1 Gigahertz to 100 Gigahertz.

18. A scanning ferromagnetic resonance (FMR) measurement system, comprising:
a wafer chuck comprising a major surface configured to support a wafer under test comprising a magnetic film;
a mounting plate arranged over the wafer chuck, the mounting plate comprising an opening extending through an entire thickness of the mounting plate;
a pair of radio frequency (RF) connectors attached to a first major surface of the mounting plate directed away from the wafer chuck;
a bent waveguide transmission line (WGTL) comprising a first end and a second end attached to a first one and a second one of the pair of RF connectors, respectively, wherein at least a portion of the bent WGTL is disposed in the opening, and wherein a bottom-most tip of the bent WGTL extends past a second major surface of the mounting plate directed towards the wafer chuck;
an RF generator configured to provide an RF signal comprising a plurality of microwave frequencies to the bent WGTL; and
a magnetic pole piece arranged over the first major surface of the mounting plate and over the bottom-most tip of the bent WGTL, the magnetic pole piece being configured to generate a magnetic field simultaneous to provision of the RF signal to the bent WGTL, wherein magnetic film of the wafer under test is configured to interact with the RF signal in the bent WGTL and the magnetic field generated by the magnetic pole piece.

19. The scanning FMR measurement system of claim 18, further comprising a controller configured to move at least one of the mounting plate or the wafer chuck to bring the bottom-most tip of the bent WGTL in physical contact with a surface of the magnetic film and to maintain the physical contact between the bottom-most tip of the bent WGTL and the magnetic film while the RF signal in the bent WGTL and the magnetic field generated by the magnetic pole piece interact with the magnetic film.

20. The scanning FMR measurement system of claim 18, wherein the bent WGTL comprises at least one of a microstrip, a grounded coplanar waveguide, or a coaxial waveguide.

* * * * *